(12) United States Patent
Raja Abdul Rahman et al.

(10) Patent No.: US 8,298,334 B2
(45) Date of Patent: *Oct. 30, 2012

(54) **METHOD FOR CRYSTALLIZING *GEOBACILLUS* STRAIN T1 LIPASE POLYPEPTIDE**

(75) Inventors: Raja Noor Zaliha Raja Abdul Rahman, Selangor (MY); Abu Bakar Salleh, Selangor (MY); Mahiran Basri, Selangor (MY); Thean Chor Leow, Selangor (MY)

(73) Assignee: Universiti Putra Malaysia, Selangor (MY)

( * ) Notice: Subject to any disclaimer, the term of this patent is extended or adjusted under 35 U.S.C. 154(b) by 163 days.

This patent is subject to a terminal disclaimer.

(21) Appl. No.: 12/151,045

(22) Filed: May 1, 2008

(65) Prior Publication Data

US 2008/0311641 A1 Dec. 18, 2008

Related U.S. Application Data

(63) Continuation of application No. PCT/MY2007/000043, filed on Jun. 20, 2007.

(30) Foreign Application Priority Data

Jun. 21, 2006 (MY) ................................ PI20062931

(51) Int. Cl.
*C30B 7/00* (2006.01)
(52) U.S. Cl. ......................................................... 117/68
(58) Field of Classification Search ........................ None
See application file for complete search history.

(56) References Cited

U.S. PATENT DOCUMENTS

2006/0024789 A1* 2/2006 Rahman et al. .............. 435/69.1
2008/0201123 A1* 8/2008 Cosgrove ......................... 703/11

OTHER PUBLICATIONS

Leow et al., Biosci. Biotechnol. Biochem. 68:96-103, 2004.*
McPherson et al., Eur. J. Biochem. 189:1-23, 1990.*
Hasanuzzaman et al., Curr. Microbiol. 49:108-114, 2004.*
Leow, "Molecular Studies, Characterization and Structure Elucidation of a Thermostable Lipase from *Geobacillus* sp.", PhD thesis, Universiti Putra Malaysia, 2005, pp. i-xxiv.*
International Search Report for PCT/MY2007/000043 dated Nov. 20, 2007.

Salleh et al., 'Structural elucidation of thermostable lipase from a new species of *Geobacillus* sp. T1', Biotechnology for Sustainable Utilization of Biological Resources in the Tropics (2004) 17:495-498.
Sinchaikul et al., 'Expression, purification, crystallization and preliminary crystallographic analysis of a thermostable lipase from *Bacillus stearothermophilus* P1' Acta Crystallographica Section D Biological Crystallography (2002) D58: 182-185.
Jeong et al., 'Crystallization and preliminary X-ray analysis of a thermoalkalophilic lipase from *Bacillus stearothermophilus* L1' Acta Crystallographica Section D Biological Crystallography (2001) D57:1300-1302.
Leow T.C. et al., 'High-Temperature Crystallization of Thermostable T1 Lipase', Crystal Growth and Design (2007) 7 (2): 406-410, published on web Dec. 29, 2006.
Tyndall et al., 'Crystal Structure of a Thermostable Lipase from *Bacillus stearothermophilus* P1', Journal of Molecular Biology (2002) 323 (5): 859-869.
Jeong et al., 'Novel Zinc-binding Center and a Temperature Switch in the *Bacilllus stearothermophilus* L1 Lipase', Journal of Biological Chemistry (2002) 277 (19): 17041-17047.
Nazina et al., 'Taxonomic study of aerobic thermophilic bacilli: descriptions of *Geobacillus subterraneus* gen. nov., sp. nov. and *Geobacillus uzenensis* sp. nov. from petroleum reservoirs and transfer of *Bacillus stearothermophilus, Bacillus thermocatenulatus, Bacillus thermoleovorans, Bacillus kaustophilus, Bacillus thermoglucosidasius* and *Bacillus thermodenitrificans* to Geobacillus as the new combinations *G. stearothermophilus, G. thermocatenulatus, G. thermoleovorans, G. kaustophilus, G. thermoglucosidasius* and *G. thermodenitrificans*', International Journal of Systematic and Evolutionary Microbiology (2001) 51:433-446.
McPherson, A. crystallization of Biological Macromolecules, Cold Spring Harbor Laboratory Press: New York, 1999.
Gernert, G.M.; Smith, R.;Carter, D.C. *Anal. Biochem.* 1988,168,141-147.
Juárez-Martínez,G. ;Garza,C. ;Castillo,R. ;Moreno,A.J.Cryst. Growth 2001, 232, 119-131.
Leow Thean Chor, Molecular Studies, Characterization and Structure Elucidation of a Thermostable Lipase From *Geobacillus* Sp., Thesis submitted to the School of Graduate Studies, Universiti Putra Malaysia, Oct. 2005, 357 pages.

* cited by examiner

*Primary Examiner* — David J Steadman
(74) *Attorney, Agent, or Firm* — Maier & Maier PLLC

(57) ABSTRACT

The present invention provides a method of crystallizing of enzymes. The method is for rapidly crystallizing enzymes from impure mixtures. The method is simple and cheap, and it is compatible to industrial requirements. T1 lipase was able to form crystals at low protein concentration (2.5 mg/ml) in a day. High temperature crystallization was obtained from the method. The present invention also relates to a composition of a crystallized lipase produced from the said method.

2 Claims, 4 Drawing Sheets

METHOD FOR CRYSTALLIZING *GEOBACILLUS* STRAIN T1 LIPASE POLYPEPTIDE

RELATED APPLICATIONS

Figure 1A:
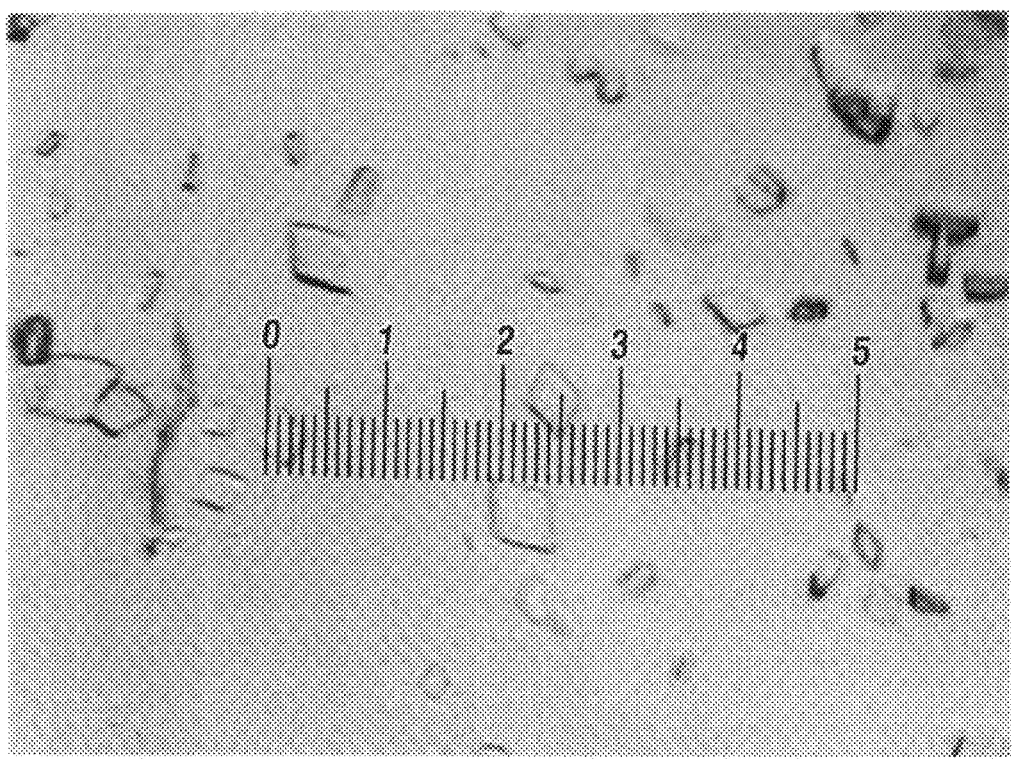

This application is a continuation of PCT Application No. PCT/MY2007/000043, filed Jun. 20, 2007, which claims priority to Malaysia Application No: P120062931, filed Jun. 21, 2006. The entire teaching of the above application is incorporated herein by reference.

FIELD OF INVENTION

The present invention encompasses crystallization and a method of crystallization of enzymes. More particularly the present invention relates to a new improved method for lipase enzyme crystallization, which is simple and cheap, and which is compatible to industrial requirements.

BACKGROUND OF INVENTION

The history of macromolecular crystal growth extends more than 150 years (a review from McPherson, 1991). Crystallization of hemoglobin from earthworm's was first observed Hünefeld in 1840 by pressing two slides of glass and allowed to dry very slowly. This revealed that protein crystals could be obtained by the controlled evaporation of a concentrated protein solution. Funke was the first person devised a successful and reproducible method for the growth of hemoglobin crystals in 1851. He described in-vitro crystallization of hemoglobin from human and animals. However, urease enzyme was crystallized by Summer, which the enzyme was exposed into 30% of acetone at cold temperature.

Crystallization of macromolecules is a complex process based on finding individual conditions and parameters leading to formation of crystal. Crystallization is one of several means by which has thermodynamic driving force that pushes the system (supersaturated solution) back to its quilibrium point reduction of salute concentration. The general processes by which substances crystallize are similar for molecules of both microscopic (salts and small molecules) and macroscopic (proteins, DNA, RNA) dimensions.

There are three stages of crystallization common to all systems such as nucleation, growth and cessation of growth. Nucleation is a process by which molecules or noncrystalline aggregates are free in solution come together to produce a thermodynamic stable aggregate with a repeating pattern. Basically in nucleation the molecules must overcome an energy barrier to form a periodically ordered aggregate or critical size.

Crystal growth generally starts at solute concentrations sufficient for nucleation to occur, and continues at concentrations beneath the nucleation threshold. The growth of crystals from nuclei is also strongly influenced by diffusion and convection effects. As with nucleation, increased protein concentration results in increased growth rates. However, in the metastable region the previously foamed nuclei will continue slowly and orderly to produce the fewest and largest single crystal. At eventually, depletion of nutrient is observed from surroundings of the single crystal.

Cessation of growth of crystals can occur for a multitude of reasons. If there should be a decrease in concentration of crystallizing solute to the point where the solid and solution phases reach exchange equilibrium. The addition of more solute can result in continued crystal growth. However, when some crystals reach a certain size beyond which growth does not proceed irrespective of salute concentration.

The complexity of crystallization problems are well presented in a schematic phase diagram of protein crystallization from McPherson, 1999 [1]

Protein crystallization is necessary for structure elucidation by X-ray diffraction. The crystallization of protein can be divided into two stages: 1) initial screening to obtain any kind of crystals or promising precipitates, and 2) optimization to improve the crystals. The appearance of crystals, even microcrystals of the smallest size or poorest quality, represents the single most important point in achieving the ultimate objective, the determination of a macromolecular structure of X-ray diffraction analysis. Thus, in the process of developing screening condition, it is desirable to create degree of supersaturation where nuclei are likely to form with reasonable concentration of protein but just below the concentration which produces uncontrollable precipitation. A sample scheme for finding optimum crystallization condition is to determine the effect of pH on precipitation with a given precipitant at various temperatures and different precipitating agents.

The ultimate goal of protein expression and purification was a single crystal that diffracts well towards structural determination through X-ray diffraction analysis. The high amount of protein with high purity (~99%) is the crucial step prior to protein crystallization. Protein expression systems available in the market simplify the basic necessity in providing sufficient yield of target protein heterologously in prokaryotic, eukaryotic or mammalian systems. As a consequence, low protein yield problem from the wild-type bacteria, particularly heat-stable lipase from *Geobacillus* spp. could be solved by manipulating gene expression. Besides, protein purification strategies are important in supplying sufficient target protein with high purity. Generally, the purification step is simplified if the targeted protein expressed as fusion protein.

Although a few lipase crystal structures of *Pseudomonas* spp., *Chromobacterium viscosum* ATCC 6918 and *Bacillus* spp. were reported so far, but none of them were derived from crystals through high temperature crystallization. It is therefore an object of the present invention, to provide a quality growth of crystal, whereby the said growth is affected by precipitants, pH, protein concentration and at high temperature.

According to the present invention, this object is solved by providing a proper selection of crystal growth conditions by precipitants, pH, protein concentration and at high temperature, wherein the affect of high temperature is possible for the growth of thermostable T1 lipase crystals.

SUMMARY OF THE INVENTION

Accordingly, it is an object of the invention to provide an improved method of producing lipase from *Geobacillus* sp strain T1. The present invention also provides a simple and low-cost method which crystallizes lipase.

It is a further object of the present invention to provide a method of crystallizing of T1 lipase, wherein the T1 lipase is T1 mature lipase and/or T1 fusion lipase.

These and other objects of the invention have been attained by the provision of a method of crystallizing T1 lipase enzyme comprising
  a. purifying T1 fusion lipase and/or T1 mature lipase,
  b. screening the T1 fusion lipase and T1 mature lipase crystals separately from step (a)

c. obtaining separately T1 fusion lipase and T1 mature lipase crystals from step (b), d. optimizing separately T1 fusion lipase and T1 mature lipase crystals condition from step (c)

In another embodiment of the invention, it is possible to obtain purified T1 lipase crystal product which has exceptional yield characteristics. The present invention also relates to a crystallization process that occurs very quickly, wherein for crystallizing lipase from *Bacillus stearothermophilus* L1 takes a week to crystallize.

BRIEF DESCRIPTION OF THE INVENTION

FIG. 1 shows effect of protein concentration on lipase crystallization a) 0. mg/ml, b) 1.0 mg/ml; (c) 2.5 mg/ml; (d) 4.5 mg/ml. The drop volume consists of 4 μl TI lipase and 2 μl mother liquor. Scale used was 1:0.1 mm.

FIG. 2 is a diagram showing T1 lipase crystallization at various temperatures (a) 16° C., (b) 20° C., (c) 40° C., (d) 50° C., (e) 60° C., (f) 70° C. The drop volume consists of 4 μl T1 lipase and 2 μl mother liquor. Scale used was 1:0.1 mm.

DETAILED DESCRIPTION OF THE INVENTION

Microbial lipases from fungi and bacterial have a significant potential for various industrial application such as detergents, oleochemistry, cheese production, pharmaceuticals and industrial synthesis of fine chemicals. Thermostable lipases isolated from thermophilic bacteria are important in industrial processes because they exhibit high thermodynamic stability at elevated temperatures and stable in organic solvents. Lipases (triacylglycerol acylhydrolases; EC 3.1.1.3) are found in various organisms, including animals, plants, fungi and bacteria. It catalyzes the hydrolysis of esters and triglycerides at interface between the insoluble substrate and water.

The ability to catalyze hydrolysis of insoluble long chain fatty acid ester in the form of micelles, small aggregates or emulsion particles distinguishes lipase from other esterase which catalyze hydrolysis of soluble esters in preference to insoluble esters. Thermostable lipases isolated from thermophilic bacteria are playing an important role in industrial processes because the thermostable lipase exhibits high thermodynamic stability at elevated temperature and in organic solvents.

T1 lipase of *Geobacillus* sp. strain T1 was expressed as GST fusion protein in *E. coli* B21(De3)pLysS harboring recombinant plasmid pGEX/TIS intracellularly. The T1 lipase was purified using Glutathione Sepharose and HiTrap Benzamidine (high sub) affinity chromatography with a final recovery and purification fold of 51.5% and 4.6, respectively. The relative molecular weight (MW) of T1 lipase was extrapolated from the known standard proteins and estimated to be 43,000 Da by Sephadex G-100 XK 16/50 gel filtration chromatography (data not shown). The molecular weight was calculated to be 43.195 kDa. However, the purified T1 lipase exhibits aggregation during concentration, as observed for other thermostable lipases such as L1 lipase and BTL2 lipase.

Small aggregates that formed during concentration were removed through centrifugation before setting up initial screening and optimization experiments. Incorporated impurities may affect the rates of growth in different directions and ultimately the shape and morphology of the crystals. During initial screening, the Crystal Screen and Crystal Screen II (Hampton research, USA) were used to screen T1 lipase crystal formation through sitting drop vapor diffusion method with an initial protein concentration of at least 0.5-4.5 mg/mL at 16-70° C. Both involved 98 well-defined conditions covering wide range of pH (4.6-9.0), additives and precipitants to provide a highly effective and rapid screening method for crystallization of macromolecules. Since an optimal condition for crystal nucleation and growth are difficult to predict. Therefore, screening is a very efficient and effective tool for determining the initial crystallization conditions of biological macromolecules.

Preliminary Crystallization of T1 Lipase

An initial screening of sitting drop vapor diffusion method involved different factors such as buffer, pH, and polymer, salt, organic and non-volatile organic to facilitate rapid searching for crystallizing condition. Izit Crystal Dye (Hampton Research, USA) was used to differentiate between protein crystals and salt crystals. When applied to T1 lipase crystal, the dye filled its solvent channels resulting in blue crystal.

Among the tested formulations, formulation 21 [0.1M $NaH_2PO_4$, 0.1M $KH_2PO_4$, 2.0M NaCl and 0.1M MES pH 6.5], 30 [0.1M HEPES pH 7.5, 10% w/v PEG6000, 5% v/v MPD] and 32[0.1M NaCl, 0.1M HEPES pH 7.5, 10% w/vPEG6000, 5% v/v MPD] and 32[0.1M NaCl, 0.1M HEPES pH 7.5, 1.6 M $(NH4)2S04$] of Crystal screen II gave better preliminary interface of small crystals of T1 lipase (0.1 mm) within one day incubation at 16° C. Formulation 21 of Crystal screen II was then chosen for optimization wherein the formulation 21 shows a reproducible and well-defined shape of crystal.

Protein and Precipitant Concentration

An optimization study was carried out with T1 lipase at various protein concentration (0.5, 1.0, 2.5. and 4.5 mg/ml) and precipitant (2 M and 1M) as variable factors for protein crystallization at 16° C. to obtain bigger and good crystals. At a lower protein concentration (0.5 and 1.0 mg/ml), 2 M of precipitating reagent was used in crystallization. For higher concentration of T1 lipase (2.5 and 4.5 mg/ml), precipitating reagent was diluted to 1M to avoid the formation of a heavy amorphous precipitate which might affect the crystal formation.

Figure 1B:
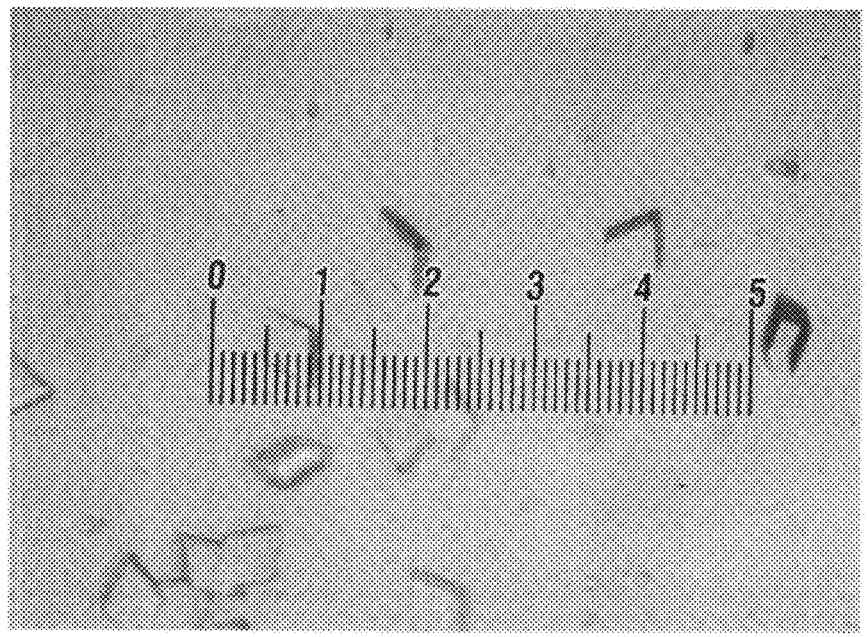
Figure 1C:
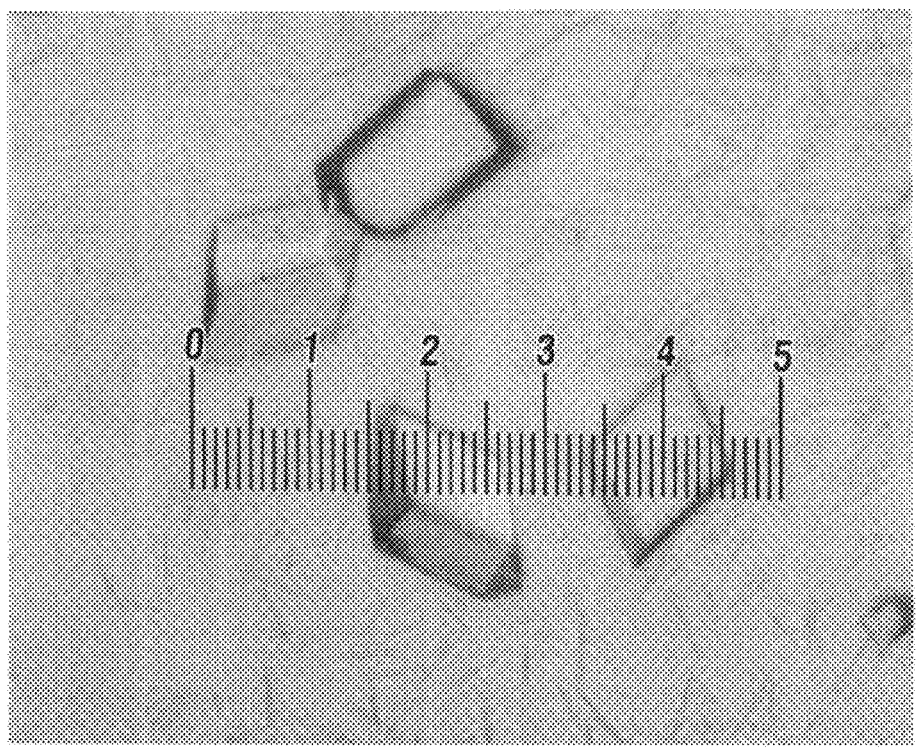
Figure 1D:
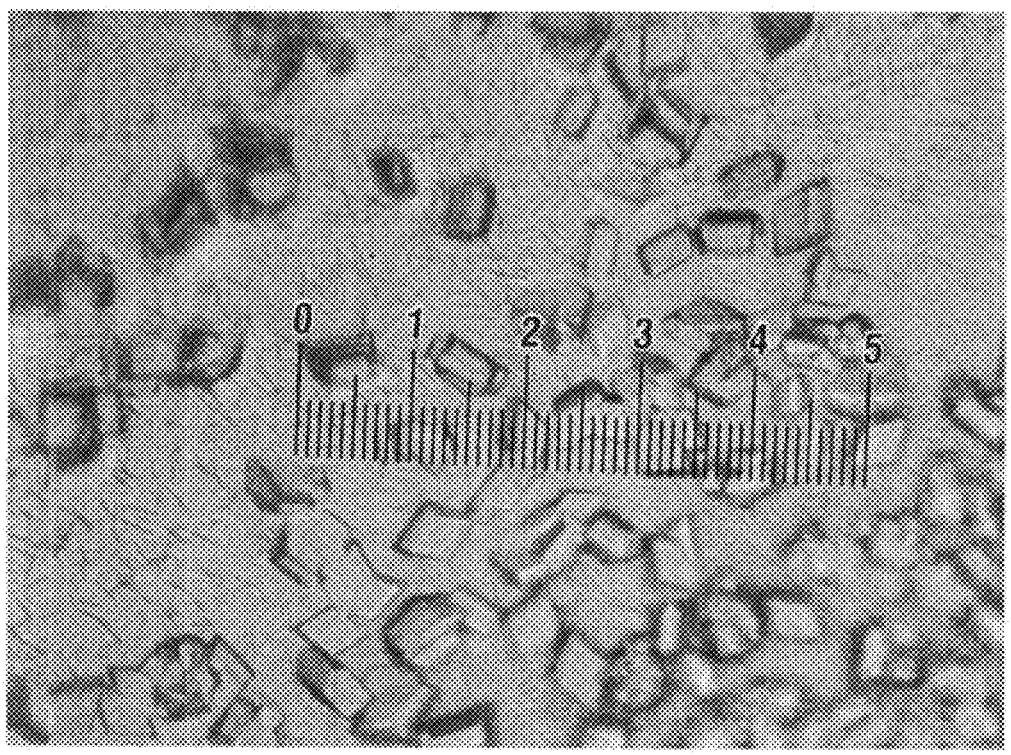

Lower concentration of TI lipase (0.5-1.0 mg/ml) formed smaller crystals even though 2.0 M NaCl was used as precipitant (FIGS. 1a & 1b). At high precipitant concentrations, crystals grow predominantly by the mechanism of two-dimensional nucleation due to limited protein. The concentration of protein was not sufficient to promote the growth of bigger size crystals even though a high concentration of precipitant (2 M NaCl) was used to crystallize the T1 lipase. However, higher concentration (2.5 mg/mL and above) of protein in combination with lower precipitant concentration (1M NaCl) promote the formation of bigger crystal at the same temperature (FIG. 1c).

Based on research relating to lipase of *Bacillus stearothermophilus* L1 was crystallized at 2.5 mg/ml within a week with 0.9 M sodium formate as precipitant at pH 4.6. However, in the present invention the T1 lipase having a similar concentration formed crystals in just a day. With regards to this, the inventors have provided a solution to save time by obtaining crystals within a day. This would help in better productivity when it is applied to relevant industries.

At higher concentration of T1 lipase (4.5 mg/ml), higher number of crystals was obtained but smaller in size due to limited space and high rate of nuclei formation to allow bigger crystal formation. In addition, this smaller size of crystals competed for the limited amount of protein for growth. Controlling the level of supersaturation throughout the crystallization process is essential if crystal size is to be optimized for the purpose of producing large, well-formed crystals for X-ray crystallographic structure determination According to Gernert et al. (1988), maintaining lower levels of supersaturation led to fewer protein crystals of a larger size than crystals grown in highly supersaturated conditions.

The function of NaCl as precipitant in the crystallization drop is to alter the protein-solvent or protein-protein contacts through water competition. Acceptable NaCl concentration allows the protein molecules to precipitate out of solution as ordered crystals and not as disordered aggregates. The formation of amorphous precipitate was reduced by lowering the ionic strength of the precipitant (NaCl) from 2.0 M to 1.0 M, when 2.5 and 4.5 mg/mL of T1 lipase were used during optimization study. However, the more concentrated the solution, the greater the supersaturation and the faster the nucleation will be since the nuclei were formed spontaneously and eventually formed many of smaller size crystals as encountered with 4.5 mg/ml T1 lipase.

FIG. 1 shows effect of protein concentration on lipase crystallization a) 0.5 mg/ml, b) 1.0 mg/ml; (c) 2.5 mg/ml; (d) 4.5 mg/ml. The drop volume consists of 4 µl TI lipase and 2 µl mother liquor. Scale used was 1:0.1 mm.

Temperature

Proteins may vary in solubility and sensitivity as a function of temperature. In addition, temperature dependence may be a function of the concentration of other mother liquor components or of ionic strength. From literature, there was no record on high temperature crystallization especially for thermostable lipases.

Temperature is being recognized as a noninvasive control parameter for protein crystallization, as compared to other parameters such as protein concentration, precipitants, buffer and pH. Temperature can be used as an alternative route in protein crystallization to precisely control the nucleation and post nucleation crystal growth without manipulation of crystallization solution towards high quality crystals. T1 lipase is a thermostable enzyme, therefore an attempt was made to crystallize T1 mature lipase at temperatures ranging from 16 to 70° C. to investigate the crystal growth range and sizes. As shown in FIG. 2, crystallization of T1 mature lipase was possible up to 60° C.

Heat inactivation tends to unfold the T1 lipase and the resulted protein may loss the conformational stability of the folded state. The needed energy for transferring a molecule from a fixed point in the solution to a fixed point to the crystal is very low. Therefore, proper selection of crystal growth temperature is important in determining the quality, size and diffractively of a crystal at optimal value.

Figure 2A:
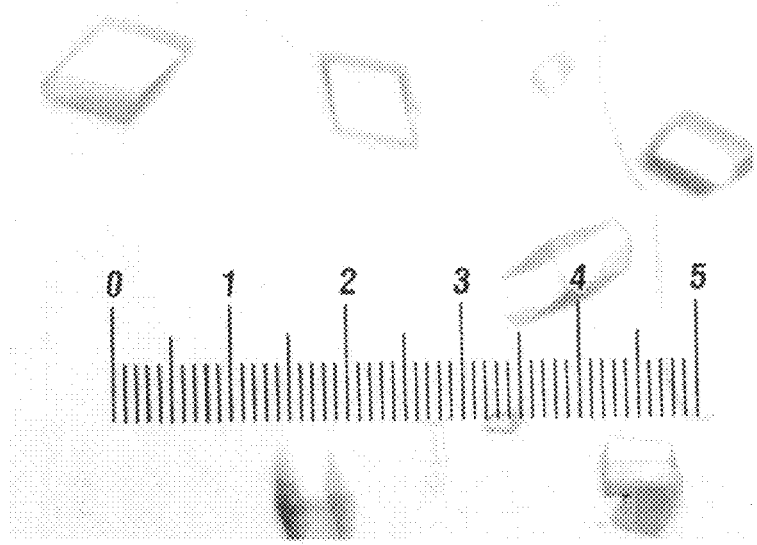
Figure 2B:
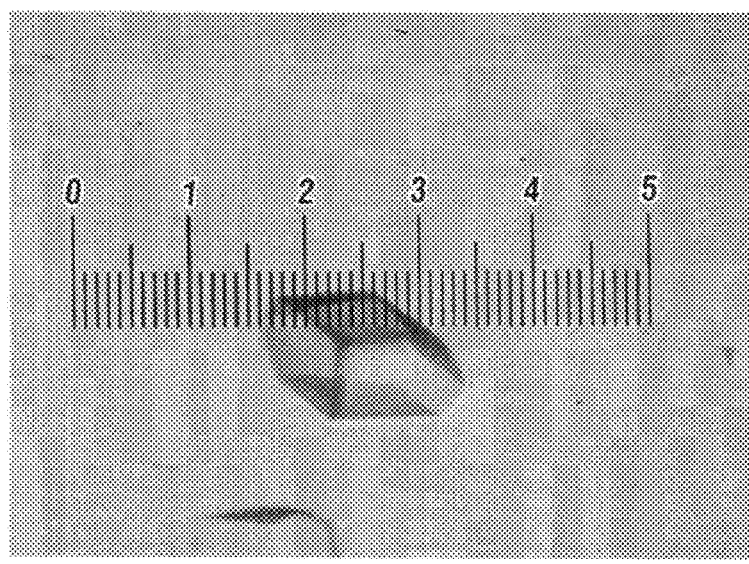
Figure 2C:
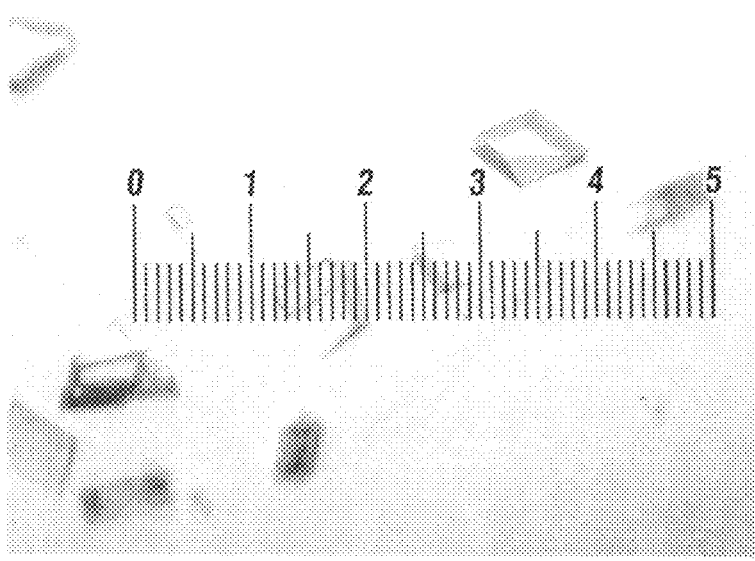
Figure 2D:
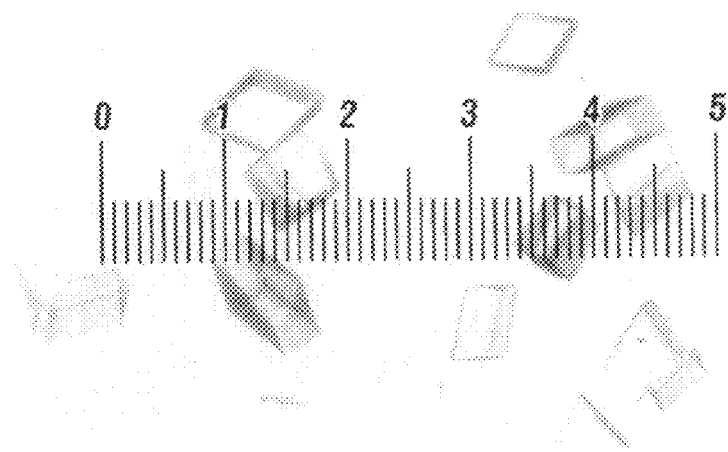
Figure 2E:
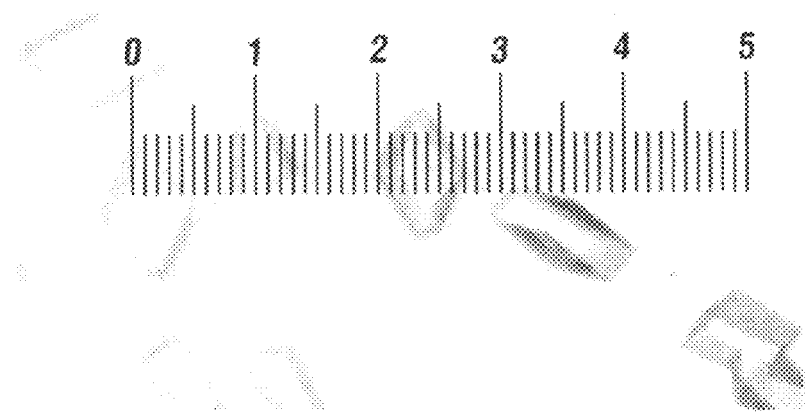
Figure 2F:
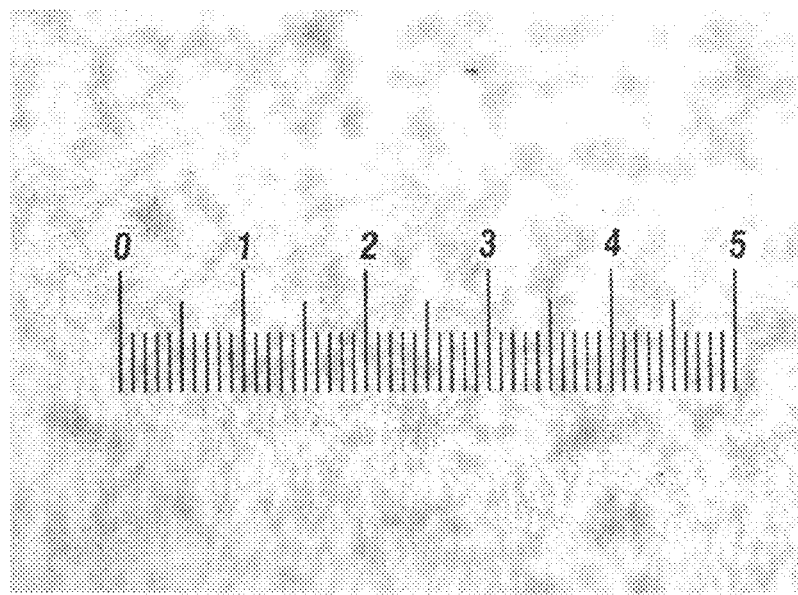

Among the tested temperatures, relatively bigger crystals (0.2 mm×0.1 mm×0.1 mm) were obtained at 20° C., as compared to other tested temperatures (FIG. 2b). Smaller size crystals obtained at higher temperatures may be due to increases in flexibility of molecules and eventually affect crystal packing as the temperature was increased. However, Jmirez-Martinez reported the no optical significant difference between the crystals that grew at 4° C. had substantially better structural quality than those grown at 18° C.

As T1 lipase crystals formed within 24 hour for all the tested temperatures, temperature was not a crucial parameter in obtaining protein crystals but it might act as a role in determining the quality of a crystal. A small increase in temperature may promote better resolution of crystal because a limited flexibility of macromolecular surfaces in allowing a better protein-protein contact and slow packing rate. However, temperatures above the optimum might significantly reduce the size and quality of a crystal as denatured protein might pack together and further reduce the resolution of a crystal.

It is to be understood that while the invention has been described in conjunction with the preferred specific embodiments thereof, the foregoing description is intended to illustrate and not limit the scope of invention.

EXAMPLES

Lipase Preparation

The structural gene corresponding to the T1 mature lipase was overexpressed in *Escherichia coli* BL21 (De3)pLysS harbouring recombinant plasmid pGEX/T1S. The fusion lipase was purified using Glutathione Sepharose HP affinity chromatography. The fusion protein was subjected to thrombin cleavage at 16° C. for 20 hour. The GST tag and thrombin enzyme were further removed by using Glutahione-Sepharose HP, HiTrap Glutathione-Sepharose 4FF and HiTrap Benzamidine in series after subjected to Sephadex G-25 gel filtration chromatography to exchange buffer and remove glutathione. The purified T1 lipase was concentrated and buffer-exchanged with 5,000 MWCO cut-off vivaspin 15R (Vivascience, Germany) to yield desired concentration of T1 lipase in 10 mM Tris-HCl (pH 8.5).

Protein Crystallization of T1 Lipase

The purified T1 lipase was crystallized through hanging and sitting drop methods with Crystal Screen and Crystal Screen II (Hampton research, USA). Parameters such as precipitant, protein concentration, and temperature were performed for crystal screening and optimization.

Precipitating Reagent

Crystal screen and crystal screen II were used as initial screening of protein crystals. The precipitating reagents (100 µl) were placed into each well in crystal clear strip. The sitting drop volume was prepared by mixing 4 µl of T1 lipase (0.5 mg/mL) in 10 mM Tris-HCl (pH 8.5) with 2 µl of mother liquor and incubated at 16° C. for few days.

Lipase Concentration

Different concentrations of T1 lipase (0.5, 1.0, 2.5 and 4.5 mg/mL) in 10 mM Tris-HCl buffer (pH 8.5) were tested for protein crystallization with hanging drop vapor diffusion method at 16° C. for few days. The drop volume was prepared by mixing 4 µl of T1 lipase with 2 µl of mother liquor with NaCl (2M or 1M) as precipitant in precipitating reagent (1 ml).

Temperature

For the effect of temperature, 16, 20, 40, 50, 60 and 70° C. were tested with T lipase at a concentration of 2.5 mg/mL (pH 8.5) through hanging drop vapor diffusion method. The drop volume was prepared by mixing 4 µl of 2.5 mg/mL T1 mature lipase with 2 µl of mother liquor with 1M NaCl as precipitant in precipitating reagent (1 ml).

Denatured Protein Analysis

The circular dichroism (CD) spectra were recorded using a J-810 spectropolarimeter (JASCO, Japan). The variable temperature measurement of T1 lipase was performed by employing 10 mm cell after checking the CD value at 220 nm. The warm-up period was 50 to 95° C., and the step was 1 degree per minute. The wavelength was set to 220 nm. The concentration was 1 mg/mL and top of the mm cell was completely closed using a cap. Data pitch, bandwidth, response, scanning speed, and accumulation were set to be 0.1 degree, 1 nm, 8 seconds, 1 degree per minute, 8 times, respectively.

REFERENCES CITED

1. McPherson, A. crystallization of Biological Macromolecules, Cold Spring Harbor Laboratory Press: New York, 1999.

2. Gemert, G. M.; Smith, R.; Carter, D. C. Anal Biochem. 1988, 168, 141-147.
3. Juárez-Martinez, G.; Gaaza, C.; Castillo R.; Moreno, A. J. Cryst. Growth 2001, 232, 119-131.

The invention claimed is:

1. A method of crystallizing T1 lipase from *Geobacillus* sp. strain T1, wherein the method comprises the following steps:
   a. Providing purified mature T1 lipase from *Geobacillus* sp. strain T1 to be crystallized, wherein said purified mature T1 lipase is prepared by expressing a T1 lipase gene in plasmid pGEX/T1S as a Glutathione-S-Transferase (GST) fusion protein, cleaving the expressed GST fusion protein by thrombin, and purifying said mature T1 lipase from GST and thrombin, wherein said purified mature T1 lipase has an estimated molecular weight of 43,000 Da;
   b. Preparing a crystallization mix comprising a buffer comprising 1 to 2M NaCl, 0.1M $NaH_2PO_4$, 0.1M $KH_2PO_4$, and 1.0M MES pH 6.5, and 0.5 to 4.5 mg/mL of purified mature T1 lipase from step (a); and
   c. Obtaining T1 lipase crystals from the crystallization mix of step (b) by a hanging-drop methodology,
   wherein crystals of the lipase are formed between about 1 hour and 1 day.

2. The method of claim 1, wherein the method is performed at a temperature of between 16° C. and 70° C.

* * * * *